United States Patent [19]

Sakane et al.

[11] Patent Number: 5,187,160
[45] Date of Patent: * Feb. 16, 1993

[54] NEW CEPHEM COMPOUND

[75] Inventors: Kazuo Sakane; Kohji Kawabata; Kenzi Miyai, all of Kawanishi; Yoshiko Inamoto, Toyonaka, all of Japan

[73] Assignee: Fujisawa Pharmaceutical Co., Ltd., Osaka, Japan

[*] Notice: The portion of the term of this patent subsequent to Aug. 28, 2007 has been disclaimed.

[21] Appl. No.: 483,646

[22] Filed: Feb. 23, 1990

[30] Foreign Application Priority Data

Mar. 8, 1989 [GB] United Kingdom ............... 8905301

[51] Int. Cl.$^5$ .................. C07D 501/46; A61K 31/545
[52] U.S. Cl. ............................. 514/202; 540/222
[58] Field of Search .................. 540/222; 514/202

[56] References Cited

U.S. PATENT DOCUMENTS 4,927,818  5/1990  Takaya et al. .............. 514/202
4,952,578  8/1990  Sakane et al. .............. 540/222

FOREIGN PATENT DOCUMENTS 223246A  5/1987  European Pat. Off. .

*Primary Examiner*—Nicholas S. Rizzo
*Attorney, Agent, or Firm*—Oblon, Spivak, McClelland, Maier & Neustadt

[57] ABSTRACT

The invention relates to antimicrobial compounds of the formula:

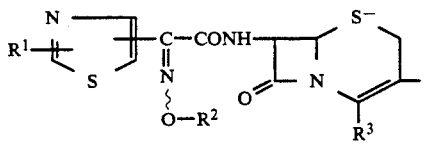

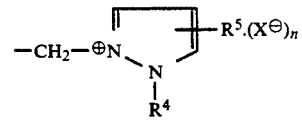

wherein $R^1$ is amino or a protected amino,
  $R^2$ is ethyl, propyl or lower alkenyl,
  $R^3$ is $COO^\ominus$, carboxy or a protected carboxy,
  $R^4$ is hydroxy(lower)alkyl or protected hydroxy(lower)alkyl,
  $R^5$ is amino or a protected amino,
  $X^\ominus$ is an anion, and
  n is 0 or 1, or, $R^1$, $R^3$, $R^5$, $X^\ominus$ and n are each as defined above,
  $R^2$ is lower alkyl, and
  $R^4$ is 3-hydroxypropyl, with proviso that
  (i) when $R^3$ is $COO^\ominus$, then n is 0, and
  (ii) when $R^3$ is carboxy or a protected carboxy, then n is 1, or a pharmaceutically acceptable salt thereof.

9 Claims, No Drawings

CEPHEM COMPOUND

The present invention relates to new cephem compound and a pharmaceutically acceptable salt thereof.

More particularly, it relates to new cephem compound and a pharmaceutically acceptable salt thereof, which have antimicrobial activities, to a process for preparation thereof, to pharmaceutical composition comprising the same, and to a method for treating infectious diseases in human being or animals.

Accordingly, one object of the present invention is to provide the cephem compound and a pharmaceutically acceptable salt thereof, which are highly active against a number of pathogenic microorganisms.

Another object of the present invention is to provide a process for the preparation of the cephem compound or a salt thereof.

A further object of the present invention is to provide a pharmaceutical composition comprising, as an active ingredient, said cephem compound or a pharmaceutically acceptable salt thereof.

Still further object of the present invention is to provide a method for treating infectious diseases caused by pathogenic microorganisms, which comprises administering said cephem compound to infected human being or animals.

The object cephem compound is novel and can be represented by the following general formula [I]:

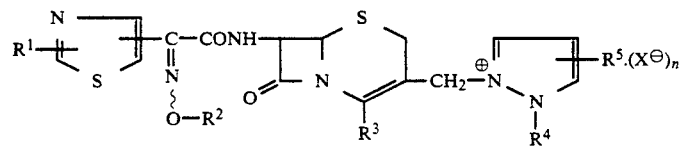

[I]

wherein
R$^1$ is amino or a protected amino,
R$^2$ is ethyl, propyl or lower alkenyl,
R$^3$ is COO$\ominus$, carboxy or a protected carboxy,
R$^4$ is hydroxy(lower)alkyl or protected hydroxy(lower)alkyl,
R$^5$ is amino or a protected amino,
X$\ominus$ is an anion, and
n is 0 or 1,
or,
R$^1$, R$^3$, R$^5$, X$\ominus$ and n are each as defined above,
R$^2$ is lower alkyl, and
R$^4$ is 3-hydroxypropyl,
with proviso that
(i) when R$^3$ is COO$\ominus$, then n is 0, and
(ii) when R$^3$ is carboxy or a protected carboxy, then n is 1.

As to the object compound [I], the following points are to be noted.

That is, the object compound [I] includes syn isomer, anti isomer and a mixture thereof. Syn isomer means one geometrical isomer having the partial structure represented by the following formula:

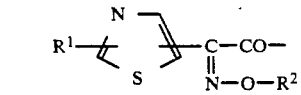

(wherein R$^1$ and R$^2$ are each as defined above), and anti isomer means the other geometrical isomer having the partial structure represented by the following formula:

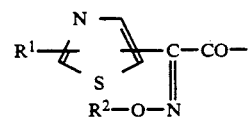

(wherein R$^1$ and R$^2$ are each as defined above , and all of such geometrical isomers and mixture thereof are included within the scope of this invention.

In the present specification and claim, the partial structure of these geometrical isomers and mixture thereof are represented for convenient sake by the following formula:

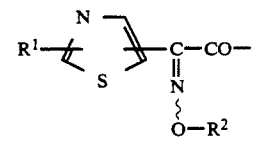

(wherein R$^1$ and R$^2$ are each as defined above).

Another point to be noted is that the pyrazolio moiety of the compound [I] can also exist in the tautomeric form, and such tautomeric equilibrium can be represented by the following scheme.

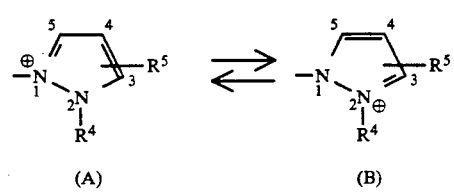

(A)        (B)

(wherein R$^4$ and R$^5$ are each as defined above).

Both of the above tautomeric isomers are included within the scope of the present invention, and in the present specification and claim, however, the object compound [I] is represented for the convenient sake by one expression of the pyrazolio group of the formula (A).

The cephem compound [I] of the present invention can be prepared by the process as illustrated in the following reaction scheme.

Process 1

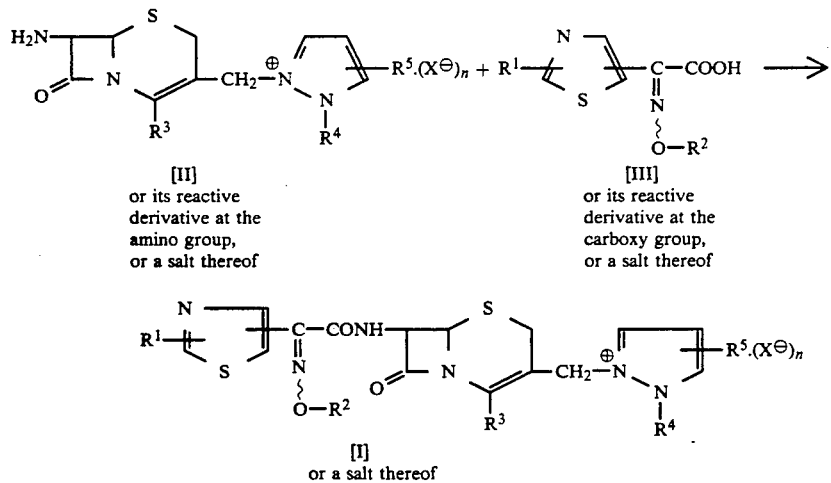

wherein $R^1$, $R^2$, $R^3$, $R^4$, $R^5$, $X^\ominus$ and n are each as defined above.

The starting compound [II] or a salt thereof is novel and can be prepared according to the following reaction schemes.

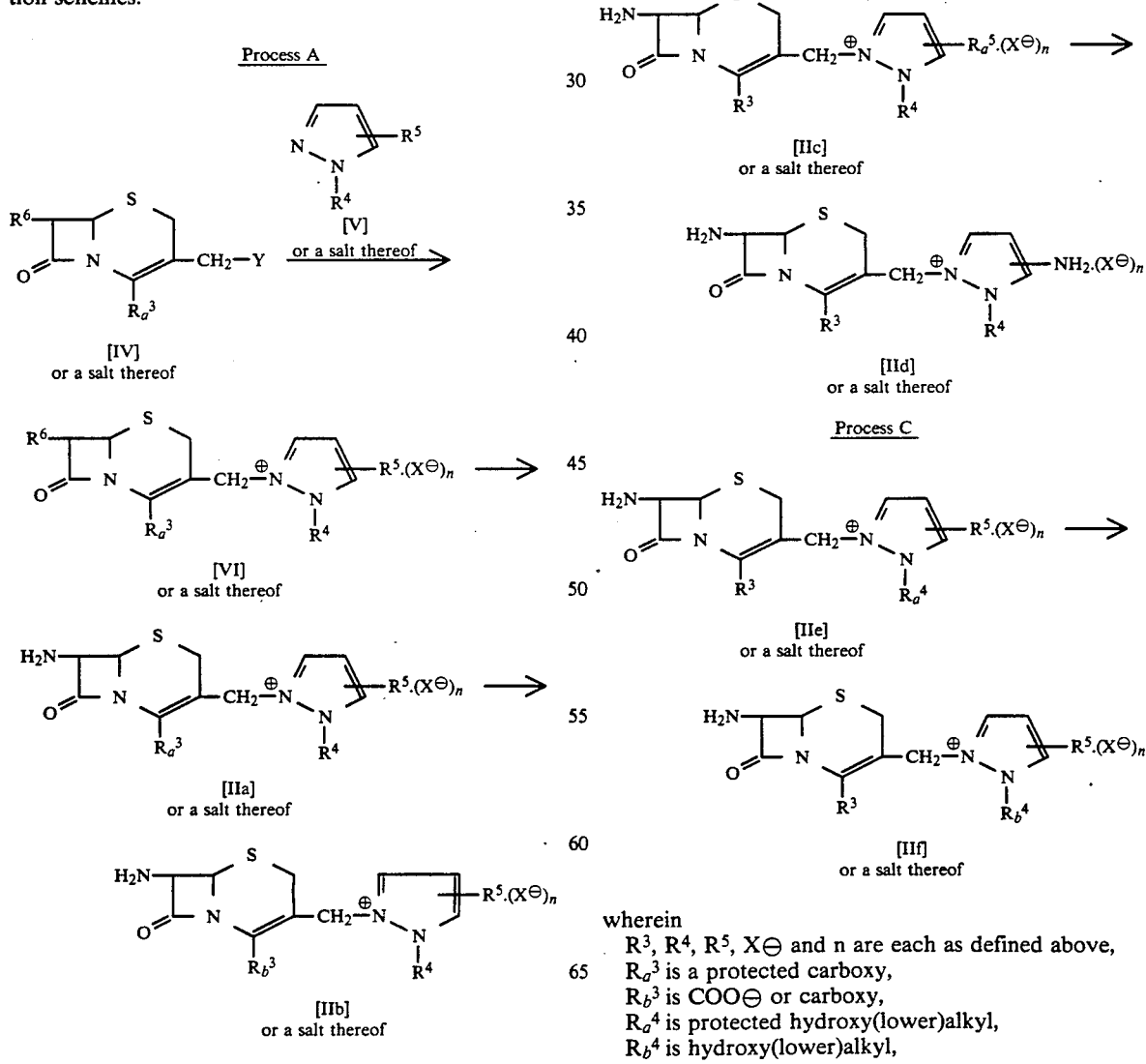

wherein
$R^3$, $R^4$, $R^5$, $X^\ominus$ and n are each as defined above,
$R_a^3$ is a protected carboxy,
$R_b^3$ is $COO^\ominus$ or carboxy,
$R_a^4$ is protected hydroxy(lower)alkyl,
$R_b^4$ is hydroxy(lower)alkyl, $R_a^5$ is a protected amino,
$R^6$ is a protected amino, and
Y is a leaving group.

Some of the starting compound [V] or a salt thereof are novel and they can be prepared according to the methods disclosed in Preparations described later or similar manners thereto.

Suitable pharmaceutically acceptable salts of the object compound [I] are conventional non-toxic mono or di salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydroiodide, sulfate, phosphate, etc.], a salt with an amino acid [e.g. arginine salt, aspartic acid salt, glutamic acid salt, etc.], and the like.

In the above and subsequent descriptions of this specification, suitable examples of the various definitions are explained in detail as follows:

The term "lower" is intended to mean 1 to 6 carbon atom(s), unless otherwise indicated.

Suitable protective group in "a protected amino" may include ar(lower)alkyl such as mono or di or triphenyl(lower)alkyl [e.g. benzyl, phenethyl, 1-phenylethyl, benzhydryl, trityl, etc.], acyl as explained hereinbelow, and the like.

Suitable acyl may be aliphatic acyl, aromatic acyl, arylaliphatic acyl and heterocyclic-aliphatic acyl derived from carboxylic acid, carbonic acid, carbamic acid, sulfonic acid, and the like.

Suitable example of the acyl group thus explained may be lower alkanoyl [e.g. formyl, acetyl, propionyl, hexanoyl, pivaloyl, etc. , mono(or di or tri)-halo(lower-)alkanoyl [e.g. chloroacetyl, trifluoroacetyl, etc.], lower alkoxycarbonyl [e.g. methoxycarbonyl, ethoxycarbonyl, tert-butoxycarbonyl, tert-pentyloxycarbonyl, hexyloxycarbonyl, etc.], mono(or di or tri)halo(lower)-alkoxycarbonyl [e.g. chloromethoxycarbonyl, dichloroethoxycarbonyl, trichloroethoxycarbonyl, etc.], aroyl [e.g. benzoyl, toluoyl, xyloyl, naphthoyl, etc.], ar(lower)alkanoyl such as phenyl(lower)alkanoyl [e.g. phenylacetyl, phenylpropionyl, etc.], aryloxycarbonyl [e.g. phenoxycarbonyl, naphthyloxycarbonyl, etc.], aryloxy(lower)alkanoyl such as phenoxy(lower)alkanoyl [e.g. phenoxyacetyl, phenoxypropionyl, etc.], arylglyoxyloyl [e.g. phenylglyoxyloyl, naphthylglyoxyloyl, etc.], ar(lower)alkoxycarbonyl which may have suitable substituent(s) such as phenyl(lower)alkoxycarbonyl which may have nitro or lower alkoxy [e.g. benzyloxycarbonyl, phenethyloxycarbonyl, p-nitrobenzyloxycarbonyl, p-methoxybenzyloxycarbonyl, etc.], thienylacetyl, imidazolylacetyl, furylacetyl, tetrazolylacetyl, triazolylacetyl, thiadiazolylacetyl, thienylpropionyl, thiadiazolylpropionyl, lower alkylsulfonyl [e.g. methylsulfonyl, ethylsulfonyl, propylsulfonyl, isopropylsulfonyl, pentylsulfonyl, butylsulfonyl, etc.], arylsulfonyl [e.g. phenylsulfonyl, tolylsulfonyl, xylylsulfonyl, naphthylsulfonyl, etc.], ar(lower)-alkylsulfonyl such as phenyl(lower)alkylsulfonyl [e.g. benzylsulfonyl, phenethylsulfonyl, benzhydrylsulfonyl, etc.], and the like.

Preferable example of "a protected amino" thus defined may be lower alkanoylamino and lower alkoxycarbonylamino, more preferable one may be ($C_1$-$C_4$)alkanoylamino and($C_1$-$C_4$)alkoxycarbonylamino, and the most preferable one may be formamido and tert-butoxycarbonylamino.

Suitable "a protected carboxy" may be an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc.], lower alkanesulfonyl(lower)alkyl ester [e.g. 2-mesylethyl ester, etc.] or mono(or di or tri)halo(lower-)alkyl ester [e.g. 2-iodoethyl ester, 2,2,2-trichloroethyl ester, etc.]; lower alkenyl ester [e.g. vinyl ester, allyl ester, etc.]; lower alkynyl ester [e.g. ethynyl ester, propynyl ester, etc.]; ar(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc.]; or the like, in which the preferred one may be mono or di or triphenyl($C_1$-$C_4$)alkyl ester and the most preferred one may be benzhydryl ester.

Suitable "lower alkyl" may be straight or branched ones such as methyl, ethyl, propyl, isopropyl, butyl, t-butyl, pentyl, 2-ethylpropyl, hexyl or the like, in which the preferred "lower alkyl" may be ($C_1$-$C_4$)alkyl and the most preferred one may be methyl.

Suitable "lower alkenyl" may be straight or branched ones having 2 to 6 carbon atoms such as vinyl, allyl, 1-propenyl, isopropenyl, 2-butenyl, 2-ethyl-2-propenyl, 4-pentenyl, 3-hexenyl or the like, in which the preferred one may be ($C_2$-$C_4$)alkenyl and the more preferred one may be allyl.

Suitable "hydroxy(lower)alkyl" may include hydroxymethyl, 1-hydroxyethyl, 2-hydroxyethyl, 3-hydroxypropyl, 1-(hydroxymethyl)ethyl, 1-hydroxybutyl, 1-hydroxymethyl-1-methylethyl, 3-hydroxypentyl, 3-hydroxy-2-ethylpropyl, 6-hydroxyhexyl and the like, in which the preferred one may be hydroxy($C_1$-$C_4$)alkyl and the most preferred one may be 2-hydroxyethyl.

Suitable "protected hydroxy(lower)alkyl" may include acyloxy(lower)alkyl and the like, in which suitable "acyl" moiety can be referred to the ones as exemplified for "a protected amino" before and suitable examples of said "acyloxy(lower)alkyl" may be lower alkanoyloxy(lower)alkyl [e.g. formyloxymethyl, 1-formyloxyethyl, 2-formyloxyethyl, 2-acetoxyeth-yl, 3-acetoxypropyl, 1-(propionyloxymethyl)-ethyl, 1-butyryloxybutyl, 1-hexanoyloxybutyl, 1-pivaloyloxymethyl-1-methylethyl, 3-formyloxypentyl, 3-formyloxy-2-ethylpropyl, 6-acetoxyhexyl, etc.], or the like; in which the preferred one may be ($C_1$-$C_4$)alkanoyloxy($C_1$-$C_4$)alkyl and the most preferred one may be 2-formyloxyethyl.

Suitable "anion" may be formate, acetate, trifluoroacetate, maleate, tartrate, methanesulfonate, benzenesulfonate, toluenesulfonate, chloride, bromide, iodide, sulfate, phosphate, or the like.

Suitable "a leaving group" may be halogen [e.g. chlorine, bromine, iodine, etc.], acyloxy such as sulfonyloxy [e.g. benzenesulfonyloxy, tosyloxy, mesyloxy, etc.], lower alkanoyloxy [e.g. acetyloxy, propionyloxy, etc.], or the like.

The process for preparing the object compound of the present invention is explained in detail in the following.

Process 1

The object compound [I] or a salt thereof can be prepared by reacting a compound [II] or its reactive derivative at the amino group or a salt thereof with a compound [III] or its reactive derivative at the carboxy group or a salt thereof.

Suitable reactive derivative at the amino group of the compound [II] may include Schiff's base type imino or its tautomeric enamine type isomer formed by the reaction of the compound [II] with a carbonyl compound such as aldehyde, ketone or the like; a silyl derivative formed by the reaction of the compound [II] with a silyl compound such as bis(trimethylsilyl)acetamide, mono(trimethylsilyl)acetamide, bis(trimethylsilyl)urea or the like; a derivative formed by reaction of the compound [II] with phosphorus trichloride or phosgene, and the like.

Suitable salts of the compound [II] and its reactive derivative can be referred to the ones as exemplified for the compound [I].

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid etc.] or aromatic carboxylic acid [e.g. benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl [$(CH_3)_2N^{30}=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound [III] to be used.

Suitable salts of the compound [III] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethylenek-etene-N-cyclohexylimine; diphenylketene-N-cyclohexylimine; ethoxyacetylene; 1-alkoxy-1-chloroethylene; trialkyl phosphite, ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

The reaction in Processes A to C for preparing the starting compound [II] can be carried out according to similar manners to those of Preparations disclosed later in the present specification.

Now in order to show the utility of the object compound [I], the test data on MIC (minimal inhibitory concentration) of representative compound [I] of this invention is shown in the following.

Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

Test Compound (1) Sulfuric acid salt of 7β-[2-(2-aminothiazol-4-yl)-2-ethoxyiminoacetamido]-3-[3-amino-2-(2-hydroxyethyl)-1-pyrazolio]methyl-3-cephem-4-carboxylate (syn isomer) (the compound of Example 2)

| Test Bacteria | Test Result MIC (μg/ml) Test Compound (1) |
|---|---|
| P. aeruginosa 26 | 1.56 |

For therapeutic administration, the object compound [I] and a pharmaceutically acceptable salt thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound [I] may vary from and also depend upon the age, conditions of the patient, a kind of diseases, a kind of the compound [I] to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compound [I] of the present invention may be used in treating diseases infected by pathogenic microorganisms.

The following Preparations and Examples are given for the purpose of illustrating the present invention in more detail.

Preparation 1

A mixture of acetic anhydride (11.13 ml) and formic acid (5.93 ml) was stirred at room temperature for 30 minutes. To this solution was added 5-amino-1-(2-hydroxyethyl)pyrazole (5 g) under ice-cooling, and the mixture was stirred at 30°–40° C. for 1 hour. The reaction mixture was poured into a mixture of water, tetrahydrofuran and ethyl acetate and adjusted to pH 6 with aqueous sodium bicarbonate. The organic layer was separated, and the aqueous layer was extracted with a mixture of tetrahydrofuran and ethyl acetate for three times. The organic layers were combined, dried over magnesium sulfate and evaporated in vacuo to give 5-formamido-1-(2-formyloxyethyl)pyrazole (5.18 g).

IR (Nujol): 3180, 1705, 1660 cm$^{-1}$

NMR (DMSO-d$_6$, δ): 4.21–4.61 (4H, m), 6.11 and 6.34 (1H, each d, J=3Hz), 7.47 (1H, d, J=3Hz), 8.00 (1H, s), 8.33 (1H, s)

Preparation 2

To a mixture of benzhydryl 7β-tert-butoxycarbonylamino-3-chloromethyl-3-cephem-4-carboxylate (20 g) and sodium iodide (5.82 g) in N,N-dimethylformamide (20 ml) was added 5-formamido-1-(2-formyloxyethyl)-pyrazole (21.34 g) at room temperature. After being stirred for 24 hours at the same temperature, the mixture was poured into a mixture of water and ethyl acetate. The organic layer was separated and washed with water, aqueous sodium chloride solution, and dried over magnesium sulfate. The solution was evaporated in vacuo to give benzhydryl 7β-tert-butoxycarbonylamino-3-[3-formamido-2-(2-formyloxyethyl)-1-pyrazolio]methyl-3-cephem-4-carboxylate iodide (29.6 g).

(Nujol): 1780, 1720 cm$^{-1}$

NMR (DMSO-d$_6$, δ): 1.49 (9H, s), 3.43 (2H, broads), 4.14–4.38 (2H, m), 4.52–4.73 (2H, m), 5.15 (1H, d, J=5Hz), 5.40 (2H, broad s), 5.67 (1H, dd, J=5Hz and 8Hz), 6.88 (1H, s), 7.02 (1H, d, J=3Hz), 7.18–7.52 (10H, m), 7.94 (1H, d, J=8Hz), 7.99 (1H, s), 8.27 (1H, d, J=3Hz), 8.51 (1H, broad s)

Preparation 3

To a solution of benzhydryl 7β-tert-butoxycarbonylamino-3-[3-formamido-2-(2-formyloxyethyl)-1-pyrazolio]-methyl-3-cephem-4-carboxylate iodide (29.5 g) and anisole (30 ml) in methylene chloride (90 ml) was added dropwise trifluoroacetic acid (60 ml) under ice-cooling. After being stirred for 1 hour at room temperature, the mixture was poured into a mixture of diisopropyl ether (600 ml) and ethyl acetate (600 ml). The resultant precipitate was collected by filtration to give bis(trifluoroacetic acid salts) of 7β-amino-3-[3-formamido-2-(2-formyloxyethyl)-1-pyrazolio]methyl-3-cephem-4-carboxylate (22.7 g).

IR (Nujol): 1780, 1715, 1660 cm$^{-1}$

NMR (DMSO-d$_6$, δ): 3.53 (2H, broad s), 4.28–4.56 (2H, m), 4.78–4.99 (2H, m), 5.29 (2H, broad s), 5.53 (2H, broad s), 7.14 (1H, d, J=3Hz), 8.22 (1H, s), 8.46 (1H, d, J=3Hz), 8.63 (1H, s)

Preparation 4

Concentrated hydrochloric acid (5.67 ml) was added to a mixture of bis(trifluoroacetic acid salts) of 7β-amino-3-[3-formamido-2-(2-formyloxyethyl)-1-pyrazolio]-methyl-3-cephem-4-carboxylate (10 g) in methanol (50 ml) at room temperature. After being stirred at the same temperature for 3 hours, the mixture was added dropwise to ethyl acetate (500 ml). The resultant precipitate was collected by filtration to give 7β-amino-3-[3-amino-2-(2-hydroxyethyl)-1-pyrazolio]-methyl-3-cephem-4-carboxylate trihydrochloride (6.1 g).

IR (Nujol): 3250, 1770, 1700, 1625 cm$^{-1}$

NMR (DMSO-d$_6$, δ): 3.43 (2H, broad s), 3.52–3.88 (2H, m), 4.18–4.48 (2H, m), 5.28 (2H, broad s), 5.37 (2H, broad s), 5.97 (1H, d, J=3Hz), 8.18 (1H, d, J=3Hz)

Preparation 5

7β-Amino-3-[3-amino-2-(2-hydroxyethyl)-1-pyrazolio ]-methyl-3-cephem-4-carboxylate trihydrochloride (66 g) was dissolved in water (264 ml). The aqueous solution was subjected to column chromatography on "Diaion HP-20" (Trademark: manufactured by Mitsubishi Chemical Industries) using water as eluent. Fractions containing the object compound were combined and to this combined solution was added dropwise isopropyl alcohol (1.15 l) under ice-cooling. The mixture was stirred for 1.5 hours under ice-cooling to precipitate crystals. The crystals were collected by filtration and washed with a mixture of isopropyl alcohol and water (10:1) under ice-cooling and dried over phosphorus pentoxide to give 7β-amino-3-[3-amino-2-(2-hydroxyethyl)-1-pyrazolio]methyl-3-cephem-4-carboxylate.hydrochloride.dihydrate (29.95 g).

IR (Nujol): 3270, 1790, 1560–1635 cm$^{-1}$

NMR (DMSO-d$_6$, δ) 3.43–3.77 (2H, m), 4.47–5.07 (4H, m), 5.07 (1H, d, J=5Hz), 5.12 and 5.38 (2H, ABq, J=16Hz), 5.92 (1H, d, J=3Hz), 7.56 (2H, broad s), 8.11 (1H, d, J=3Hz)

Analysis (%) Calcd. for C$_{13}$H$_{17}$N$_5$O$_4$S.HCl.2H$_2$O: C 37.90, H 5.38, N 17.00, Cl 8.60
Found: C 37.82, H 5.56, N 16.73, Cl 8.60

Preparation 6

Methyl acrylate (43.34 ml) was added to 5-aminopyrazole (30 g) with stirring at room temperature. The mixture was stirred at 90° C. for one hour.

The reaction mixture was cooled and evaporated under reduced pressure.

The residue (66 g) was subjected to column chromatography on silica gel (3 l) and eluted with ethyl acetate. The fractions containing the object compound were combined and concentrated under reduced pressure to give 5-amino-1-(2-methoxycarbonylethyl)pyrazole (10.7 g).

IR (Neat): 3340, 3200, 1720, 1560, 1440, 1220 cm$^{-1}$
NMR (DMSO-d$_6$, δ) 2.75 (2H, t, J=7Hz), 3.60 (3H, s), 4.06 (2H, t, J=7Hz), 5.08 (2H, s), 5.25 (1H, d, J=2Hz), 7.00 (1H, d, J=2Hz)

Preparation 7

A solution of 5-amino-1-(2-methoxycarbonylethyl)-pyrazole (10.7 g) in tetrahydrofuran (80 ml) was added dropwise to a suspension of lithium aluminum hydride (7.20 g) in tetrahydrofuran (120 ml) with stirring and ice-cooling.

The mixture was stirred for two hours, and sodium fluoride (31.87 g) was added thereto. The mixture was cooled to 0°~5° C. in an ice-bath and water (10.26 ml) was added dropwise thereto. An insoluble material was filtered off and the filtrate was evaporated under reduced pressure to give 5-amino-1-(3-hydroxypropyl)-pyrazole (5.36 g).

IR (Nujol): 3300, 3150, 1640, 1550, 1070, 1020, 740 cm$^{-1}$
NMR (DMSO-d$_6$, δ): 1.81 (2H, quintet, J=6Hz), 4.55 (1H, s), 5.01 (2H, s), 5.24 (1H, d, J=2Hz), 6.99 (1H, d, J=2Hz)

Preparation 8

5-Amino-1-(3-hydroxypropyl)pyrazole (5.3 g) was added to a mixture of acetic anhydride (8.86 ml) and formic acid (7.08 ml) under ice-cooling. The mixture was stirred for two hours at room temperature. The reaction mixture was added to a mixture of ice-water (30 ml), ethyl acetate (30 ml) and tetrahydrofuran (60 ml), and an aqueous solution of potassium carbonate was added thereto to adjust the pH of the mixture to 7. The organic layer was separated and dried over magnesium sulfate. The magnesium sulfate was filtered off, and the filtrate was evaporated under reduced pressure to give 5-formamido-1-(3-formyloxypropyl)pyrazole (6.74 g).

IR (Nujol): 3200, 1700, 1660, 1550, 1200, 1160, 890, 790 cm$^{-1}$
NMR (DMSO-d$_6$, δ): 2.05 (2H, quintet, J=6Hz), 4.07 (4H, t, J=6Hz), 6.25 (1H, d, J=2Hz), 7.33 (1H, d, J=2Hz), 8.14 (1H, s), 8.21 (1H, s)

Preparation 9

Benzhydryl 7β-tert-butoxycarbonylamino-3-chloromethyl-3-cephem-4-carboxylate (5.87 g) was added to N,N-dimethylformamide (5.87 ml) with stirring. Sodium iodide (1.71 g) was added thereto, followed by addition of 5-formamido-1-(3-formyloxypropyl)pyrazole (6.74 g). The mixture was stirred for 24 hours at room temperature.

The reaction mixture was added to a mixture of ethyl acetate (230 ml) and ice-water (115 ml). The organic layer was separated washed with sodium chloride aqueous solution and dried over magnesium sulfate. The magnesium sulfate was filtered off, and the filtrate was concentrated under reduced pressure to 60 ml. The residue was pulverized with diisopropyl ether (500 ml) to give benzhydryl 7β-tert-butoxycarbonylamino-3-[3-formamido-2-(3-formyloxypropyl)-1-pyrazolio]methyl-3-cephem-4-carboxylate iodide.

NMR (DMSO-d$_6$, δ): 1.43 (9H, s), 2.06 (2H, quintet, J=6Hz), 3.46 (2H, broad s), 4.06 (2H, t, J=6Hz), 4.08 (2H, t, J=6Hz), 5.16 (1H, d, J=5Hz), 5.40 (2H, s), 5.60 (1H, dd, J=8Hz and 5Hz), 6.89 (1H, s), 7.00 (1H, d, J=3Hz), 7.95 (1H, d, J=8Hz), 7.97 (1H, s), 8.20 (1H, d, J=3Hz), 8.50 (1H, s)

Preparation 10

Benzhydryl 7β-tert-butoxycarbonylamino-3-[3-formamido-2-(3-formyloxypropyl)-1-pyrozolio]methyl-3-cephem-4-carboxylate iodide (6.50 g) was added to methylene chloride (19.5 ml) followed by addition of anisole (6.5 ml). The mixture was cooled to 0°~5° C. in an ice-bath, and then trifluoroacetic acid (13 ml) was added dropwise thereto. The mixture was stirred for 3 hours at room temperature. The reaction mixture was pulverized with a mixture of ethyl acetate (100 ml) and diisopropyl ether (100 ml) to give bis(trifluoroacetic acid salts) of 7β-amino-3-[3-formamido-2-(3-formyloxypropyl)-1-pyrozolio]methyl-3-cephem-4-carboxylte (5.30 g).

IR (Nujol): 1780, 1700 cm$^{-1}$
NMR (DMSO-d$_6$, δ): 2.06 (2H, quintet, J=6Hz), 3.50 (2H, broad s), 4.06 (4H, t, J=6Hz), 5.23 (2H, m), 5.46 (2H, s), 7.04 (1H, d, J=3Hz), 8.12 (1H, s), 8.34 (1H, d, J=3Hz), 8.53 (1H, s)

Preparation 11

Bis(trifluoroacetic acid salts) of 7β-amino-3-[3-formamido-2-(3-formyloxypropyl)-1-pyrazolio]methyl-3-cephem-4-carboxylate (5.30 g) was added to methanol (31.8 ml). Concentrated hydrochloric acid was added dropwise thereto with stirring at room temperature. The mixture was stirred for 3 hours. The reaction mixture was pulverized with ethyl acetate (400 ml) to give 7β-amino-3-[3-amino-2-(3-hydroxypropyl)-1-pyrazolio]methyl-3-cephem-4-carboxylate trihydrochloride.

IR (Nujol): 3300, 1780, 1630, 1580, 1220 cm$^{-1}$
NMR (DMSO-d$_6$, δ): 1.60–2.00 (2H, m), 3.30–3.60 (4H, m), 3.65–3.83 (2H, m), 5.23 (2H, m), 5.30 (2H, broad s), 5.92 (1H, d, J=3Hz), 8.14 (1H, d, J=3Hz)

EXAMPLE 1

A solution of 7β-amino-3-[3-amino-2-(2-hydroxyethyl)-1-pyrazolio]methyl-3-cephem-4-carboxylate hydrochloride. dihydrate (1.5 g) in a mixture of water (15 ml) and tetrahydrofuran (30 ml) was adjusted to pH 7 with saturated sodium bicarbonate aqueous solution and 2-(2-aminothiazol-4-yl)-2-ethoxyiminoacetic acid (syn isomer) activated by 1-hydroxy-1H-benzotriazole (2.22 g) was added thereto at room temperature. The mixture was stirred for 5 hours at 30° C. maintaining pH 7 with addition of 20% potassium carbonate aqueous solution. To the reaction mixture was added ethyl acetate (30 ml) and the separated aqueous layer was washed with ethyl acetate (20 ml×2). The aqueous solution was adjusted to pH 4 with 1N-hydrochloric acid and washed with ethyl acetate (20 ml×3). The aqueous solution was adjusted to pH 2 with addition of 1N hydrochloric acid and subjected to column chromatography on "Diaion HP-20" (60 ml) using aqueous isopropyl alcohol, as an eluent. Fractions containing the object compound were combined and evaporated and lyophilized to give 7β-[2-(2-aminothiazol-4-yl)-2-ethoxyiminoacetamido ]-3-[3-amino-2-(2-hydroxyethyl)-1-pyrazolio]methyl-3-cephem-4-carboxylate (syn isomer) (1.30 g).

NMR (D₂O-NaHCO₃, δ): 1.33 (3H, t, J=7Hz), 3.07 and 3 40 (2H, ABq, J=18Hz), 3.85 (2H, t, J=5Hz), 4.25 (2H, q, J=7Hz), 4.32 (2H, t, J=5Hz), 5.00 and 5.22 (2H, ABq, J=15Hz), 5.21 (1H, d, J=5Hz), 5.81 (1H, d, J=5Hz), 5.94 (1H, d, J=3Hz), 6.94 (1H, s), 7.84 (1H, d, J=3Hz)

EXAMPLE 2

To a solution of 7β-[2-(2-aminothiazol-4-yl)-2-ethoxyiminoacetamido ]-3-[3-amino-2-(2-hydroxyethyl)-1-pyrazolio]methyl-3-cephem-4-carboxylate (syn isomer) (1 g) in a mixture of water (1 ml) and 2M-sulfuric acid (1 ml) was added dropwise ethanol (1 ml) at room temperature. The mixture was stirred for 1.5 hours under the same condition to precipitate the crystals. The crystal was collected by filtration and washed with acetone to give sulfuric acid salt of 7β-[2-(2-aminothiazol-4-yl)-2-ethoxyiminoacetamido ]-3-[3-amino-2-(2-hydroxyethyl)-1-pyrazolio ]methyl-3-cephem-4-carboxylate (syn isomer) as crystals.

IR (Nujol 3230, 1775, 1670, 1645, 1590, 1550 cm⁻¹
NMR (D₂O-NaHCO₃, δ): 1.33 (3H, t, J=7Hz), 3.10 and 3.43 (2H, ABq, J=18Hz and 30Hz), 3.85 (2H, t, J=5Hz), 4.30 (2H, q, J=7Hz), 4.37 (2H, t, J=5Hz), 5.02 and 5.22 (2H, ABq, J=15Hz and 18Hz), 5 21 (1H, d, J=5Hz), 5.79 (1H, d, J=5Hz), 5.97 (1H, d, J=3Hz), 7.03 (1H, s), 7.85 (1H, d, J=3Hz)

EXAMPLE 3

7β-[2-(2-Aminothiazol-4-yl)-2-allyloxyiminoacetamido ]-3-[3-amino-2-(2-hydroxyethyl)-1-pyrazolio ]-methyl-3-cephem-4-carboxylate (syn isomer) was obtained according to a similar manner to that of Example 1.

NMR (D₂O-NaHCO₃, δ): 3.07 and 3.40 (2H, ABq, J=18Hz and 30Hz), 3.86 (2H, t, J=5Hz), 4.34 (2H, t, J=5Hz), 5.01 and 5.22 (2H, ABq, J=15Hz and 8Hz), 5.21 (1H, d, J=5Hz), 4.85-5.5 (4H, m), 5.82 (1H, d, J=5Hz), 5.95 (1H, d, J=3Hz), 5.73-6.3 (1H, m), 6.97 (1H, s), 7.85 (1H, d, J=3Hz)

EXAMPLE 4

Sulfuric acid salt of 7β-[2-(2-aminothiazol-4-yl)-2-allyloxyiminoacetamido ]-3-[3-amino-2-(2-hydroxyethyl)-1-pyrazolio ]methyl-3-cephem-4-carboxylate (syn isomer) was obtained according to a similar manner to that of Example 2.

IR (Nujol 3260, 1780, 1680, 1650, 1570, 1530 cm⁻¹.
NMR (D₂O-NaHCO₃, δ): 3.07 and 3.39 (2H, ABq, J=18Hz and 30Hz), 3.85 (2H, t, J=5Hz), 4.33 (2H, t, J=5Hz), 4.83-5.53 (6H, m), 5.20 (1H, d, J=5Hz). 5.80 (1H, d, J=5Hz), 5.96 (1H, d, J=3Hz), 5.70-6.33 (1H, m), 6.96 (1H, s), 7.85 (1H, d, J=3Hz)

EXAMPLE 5

7β-[2-(2-Aminothiazol-4-yl)-2-methoxyiminoacetamido ]-3-[3-amino-2-(3-hydroxypropyl)-1-pyrazolio]methyl-3-cephem-4-carboxylate (syn isomer) was obtained according to a similar manner to that of Example 1.

IR (Nujol): 3300, 3150, 1770, 1600, 1530, 1030 cm⁻¹
NMR (D₂O, δ): 1.95 (2H, quintet, J=6Hz), 3.15 (1H, d, J=18Hz), 3.35 (1H, d, J=18Hz), 3.60 (2H, t, J=6Hz), 4 00 (3H, s), 4.26 (2H, t, J=6Hz), 5.12 (2H, m), 5.20 (1H, d, J=5Hz), 5.80 (1H, d, J=5Hz), 5.93 (1H, d, J=3Hz), 6.96 (1H, s), 7.83 (1H, d, J=3Hz)

EXAMPLE 6

Sulfuric acid salt of 7β-12-(2-aminothiazol-4-yl)-2-methoxyiminoacetamido ]-3-[3-amino-2-(3-hydroxypropyl)-1-pyrazolio ]methyl-3-cephem-4-carboxylate (syn isomer) was obtained according to a similar manner to that of Example 2.

IR (Nujol): 3200, 1770, 1650, 1160, 1030 cm⁻¹
NMR (D₂O, δ): 1.95 (2H, quintet, J=6Hz), 3.20 (1H, d, J=18Hz), 3.40 (1H, d, J=18Hz), 3.60 (2H, t, J=6Hz), 4.05 (3H, s), 4.26 (2H, t, J=6Hz), 5.16 (2H, broad s), 5.21 (1H, d, J=5Hz), 5.79 (1H, d, J=5Hz), 5.94 (1H, d, J=3Hz), 7.07 (1H, s), 7.83 (1H, d, J=3Hz)

EXAMPLE 7

To a solution of 7β-[2-(2-aminothiazol-4-yl)-2-ethoxyiminoacetamido ]-3-[3-amino-2-(2-hydroxyethyl)-1-pyrazolio ]methyl-3-cephem-4-carboxylate (syn isomer) (300 mg) in water (15 ml) was added 1N hydrochloric acid (0.56 ml). The mixture was lyophilized to give 7β-[2-(2-aminothiazol-4-yl)-2-ethoxyiminoacetamido ]-3-[3-amino-2-(2-hydroxyethyl)-1-pyrazolio ]methyl-3-cephem-4-carboxylate hydrochloride (syn isomer) (310 mg).

IR (Nujol): 1780 640, 1590 cm⁻¹
NMR (DMSO-d₆, δ): 1.27 (3H, t, J=7Hz), 3.45–3.8 (2H, m), 4.12 (2H, q, J=8Hz), 4.10–4.90 (4H, m), 4.97–5.50 (2H, m), 5.20 (1H, d, J=5Hz), 5.82 (1H, dd, J=5Hz and 8Hz), 5.89 (1H, d, J=3Hz), 6.73 (1H, s), 7.48 (2H, broad s), 8.00 (1H, d, J=3Hz), 9.54 (1H, d, J=8Hz)

EXAMPLE 8

7β-[2-(2-Aminothiazol-4-yl)-2-allyloxyiminoacetamido ]-3-[3-amino-2-(2-hydroxyethyl)-1-pyrazolio ]-methyl-3-cephem-4-carboxylate hydrochloride (syn isomer) was obtained according to a similar manner to that of Example 7.

IR (Nujol): 1775, 1660, 1640, 1585, 1540 cm⁻¹
NMR (DMSO-d₆, δ): 3.43–3.77 (2H, m), 4.03–5.07 (4H, m), 4.97–5.60 (7H, m), 5.88 (1H, dd, J=5Hz and 8Hz), 5.90 (1H, d, J=3Hz), 5.80–6.27 (1H, m), 6.77 (1H, s), 7.47 (2H, broad s), 8.01 (1H, d, J=3Hz), 9.64 (1H, d, J=8Hz)

EXAMPLE 9

7β-[2-(2-Aminothiazol-4-yl)-2-propoxyiminoacetamido]3-[2-(2-hydroxyethyl)-1pyrazolio]-methyl-3-cephem-4-carboxylate (syn isomer) was obtained according to a similar manner to that of Example 1.

IR (Nujol): 3300,1760,1660,1600 cm⁻¹
NMR (D₂O-NaHCO₃, δ): 0.94 (3H, t, J=8Hz), 1.50–1.93 (2H, m), 3.10 and 3.40 (2H, ABq, J=18Hz), 3.85 (2H, t, J=5Hz), 4.16 (2H, t, J=8Hz), 4.33 (2H, t, J=5Hz), 5.08 (2H, broad s), 5.23 (1H, d, J=5Hz), 5.79 (1H, d, J=5Hz), 5.93 (1H, d, J=3Hz), 6.92 (1H, s), 7.83 (1H, d, J=3Hz)

What we claim is:
1. A cephem compound of the formula:

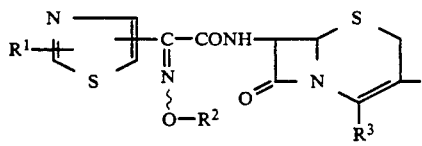

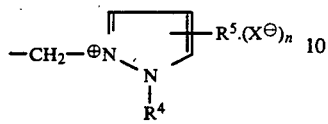

wherein
- $R^1$ is amino or a protected amino,
- $R^2$ is ethyl, propyl or lower alkenyl,
- $R^3$ is $COO^\ominus$, carboxy or a protected carboxy,
- $R^4$ is hydroxy(lower)alkyl or protected hydroxy(lower)alkyl,
- $R^5$ is amino or a protected amino,
- $X^\ominus$ is an anion, and
- n is 0 or 1, or,
- $R^1$, $R^3$, $R^5$, $X^\ominus$ and n are each as defined above,
- $R^2$ is lower alkyl, and
- $R^4$ is 3-hydroxypropyl, with proviso that
(i) when $R^3$ is $COO^\ominus$, then n is 0, and
(ii) when $R^3$ is carboxy or a protected carboxy, then n is 1,
or a pharmaceutically acceptable salt thereof.

2. A compound of claim 1, wherein
$R^2$ is ethyl or propyl.

3. A compound of claim 2, wherein
$R^1$ is amino,
$R^3$ is $COO^\ominus$,
$R^4$ is hydroxy(lower)alkyl,
$R^5$ is amino, and
n is 0.

4. A compound of claim 1, wherein
$R^2$ is lower alkenyl.

5. A compound of claim 4, wherein
$R^1$ is amino,
$R^3$ is $COO^\ominus$,
$R^4$ is hydroxy(lower)alkyl,
$R^5$ is amino, and
n is 0.

6. A compound of claim 1, wherein
$R^2$ is lower alkyl, and
$R^4$ is 3-hydroxypropyl.

7. A compound of claim 6, wherein
$R^1$ is amino,
$R^3$ is $COO^\ominus$,
$R^5$ is amino, and
n is 0.

8. An antimicrobial pharmaceutical composition which comprises, as an active ingredient, an effective amount of a compound of claim 1 or a pharmaceutically acceptable salt thereof in admixture with a pharmaceutically acceptable carrier.

9. A method for the treatment of infectious diseases which comprises administering an effective amount of a compound of claim 1 or a pharmaceutically acceptable salt thereof to a human being or animal.

* * * * *